United States Patent
Bharmi et al.

(10) Patent No.: US 8,019,410 B1
(45) Date of Patent: Sep. 13, 2011

(54) SYSTEM AND METHOD FOR DETECTING HYPOGLYCEMIA USING AN IMPLANTABLE MEDICAL DEVICE BASED ON PRE-SYMPTOMATIC PHYSIOLOGICAL RESPONSES

(75) Inventors: Rupinder Bharmi, Stevenson Ranch, CA (US); Gene A. Bornzin, Simi Valley, CA (US); Brian Jeffrey Wenzel, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 1056 days.

(21) Appl. No.: 11/843,480

(22) Filed: Aug. 22, 2007

(51) Int. Cl.
*A61B 5/0205* (2006.01)
*A61B 5/0452* (2006.01)

(52) U.S. Cl. .................................. 600/516; 600/365

(58) Field of Classification Search .............. 600/365, 600/516, 517
See application file for complete search history.

(56) References Cited

U.S. PATENT DOCUMENTS

| | | |
|---|---|---|
| 4,731,051 A | 3/1988 | Fischell |
| 4,759,366 A | 7/1988 | Callaghan |
| 4,947,845 A | 8/1990 | Davis |
| 5,113,869 A | 5/1992 | Nappholz et al. |
| 5,135,004 A | 8/1992 | Adams et al. |
| 5,148,812 A | 9/1992 | Verrier et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 5,365,426 A | 11/1994 | Siegel et al. |
| 5,400,795 A | 3/1995 | Murphy et al. |
| 5,425,749 A | 6/1995 | Adams |
| 5,520,191 A | 5/1996 | Karlsson et al. |
| 5,720,295 A | 2/1998 | Greenhut et al. |
| 5,741,211 A | 4/1998 | Renirie et al. |
| 5,785,660 A | 7/1998 | van Lake et al. |
| 5,792,065 A | 8/1998 | Xue et al. |
| 5,891,047 A | 4/1999 | Lander et al. |
| 5,960,797 A | 10/1999 | Kramer et al. |
| 6,016,443 A | 1/2000 | Ekwall et al. |
| 6,021,350 A | 2/2000 | Mathson |
| 6,038,469 A | 3/2000 | Karlsson et al. |
| 6,108,577 A | 8/2000 | Benser |

(Continued)

FOREIGN PATENT DOCUMENTS

EP 0472411 A1 2/1992

(Continued)

OTHER PUBLICATIONS

Harris, ND et al, "Can Changes in QT Interval be used to Predict the Onset of Hypoglycemia in Type 1 Diabetes?" Computers in Cardiology 2000;27:375-378.

(Continued)

*Primary Examiner* — Carl H. Layno
*Assistant Examiner* — Tammie K Heller

(57) ABSTRACT

An intracardiac electrogram (IEGM) or other suitable electrical cardiac signal is sensed. Values representative of a pre-symptomatic physiologic response to a hypoglycemic event are derived from the cardiac signal. Then, hypoglycemia is detected based on the values representative of the pre-symptomatic physiologic response. In one example, both temporal morphological parameters and spectral parameters affected by pre-symptomatic hypoglycemia are derived from the cardiac signal. Hypoglycemia is then detected based on a combination of the temporal and spectral parameters using, e.g., a linear discriminator. By detecting hypoglycemia based on parameters affected by pre-symptomatic hypoglycemia, suitable warnings can be generated and therapies initiated before the condition becomes symptomatic.

27 Claims, 9 Drawing Sheets

U.S. PATENT DOCUMENTS

| | | | |
|---|---|---|---|
| 6,112,116 | A | 8/2000 | Fischell et al. |
| 6,115,628 | A | 9/2000 | Stadler et al. |
| 6,128,526 | A | 10/2000 | Stadler et al. |
| 6,233,486 | B1 | 5/2001 | Ekwall et al. |
| 6,249,705 | B1 | 6/2001 | Snell |
| 6,256,538 | B1 | 7/2001 | Ekwall |
| 6,264,606 | B1 | 7/2001 | Ekwall et al. |
| 6,272,379 | B1 | 8/2001 | Fischell et al. |
| 6,361,503 | B1 | 3/2002 | Starobin et al. |
| 6,377,852 | B1 | 4/2002 | Bornzin et al. |
| 6,381,493 | B1 | 4/2002 | Stadler et al. |
| 6,501,983 | B1 | 12/2002 | Natarajan et al. |
| 6,572,542 | B1 | 6/2003 | Houben et al. |
| 6,622,045 | B2 | 9/2003 | Snell et al. |
| 6,731,985 | B2 | 5/2004 | Poore et al. |
| 7,010,345 | B2 | 3/2006 | Hill et al. |
| 7,016,720 | B2 | 3/2006 | Kroll |
| 7,029,443 | B2 | 4/2006 | Kroll |
| 7,076,300 | B1 | 7/2006 | Kroll et al. |
| 7,096,064 | B2 | 8/2006 | Deno et al. |
| 7,103,412 | B1 | 9/2006 | Kroll |
| 7,142,911 | B2 | 11/2006 | Boileau et al. |
| 7,272,436 | B2 | 9/2007 | Gill et al. |
| 7,297,114 | B2 | 11/2007 | Gill et al. |
| 7,813,791 | B1 * | 10/2010 | Gill et al. ............ 600/521 |
| 2002/0143266 | A1 | 10/2002 | Bock |
| 2002/0143372 | A1 | 10/2002 | Snell et al. |
| 2004/0077962 | A1 | 4/2004 | Kroll |
| 2004/0078065 | A1 | 4/2004 | Kroll |
| 2004/0138716 | A1 | 7/2004 | Kon et al. |
| 2004/0249420 | A1 | 12/2004 | Olson et al. |
| 2005/0288725 | A1 | 12/2005 | Hettrick et al. |
| 2006/0167365 | A1 | 7/2006 | Bharmi |
| 2006/0167517 | A1 | 7/2006 | Gill et al. |
| 2006/0167518 | A1 | 7/2006 | Gill et al. |
| 2006/0167519 | A1 | 7/2006 | Gill et al. |
| 2006/0247685 | A1 | 11/2006 | Bharmi |
| 2007/0118054 | A1 * | 5/2007 | Pinhas et al. ........ 600/587 |
| 2007/0287923 | A1 * | 12/2007 | Adkins et al. ........ 600/485 |

FOREIGN PATENT DOCUMENTS

| | | |
|---|---|---|
| EP | 0867146 A1 | 9/1998 |
| EP | 0867146 B1 | 2/2004 |
| EP | 1419731 A1 | 5/2004 |
| EP | 0939602 B1 | 9/2004 |
| EP | 1419731 B1 | 3/2006 |
| WO | 97/15227 | 5/1997 |
| WO | 2006081336 A2 | 8/2006 |

OTHER PUBLICATIONS

Okin, Peter M. et al, "Electrocardiographic Repolarization Complexity and Abnormality Predict All-Cause and Cardiovascular Mortality in Diabetes The Strong Heart Study," Diabetes 53:434-440, 2004.

Rana, Bushra S. et al, "Relation of QT Interval Dispersion to the Number of Different Cardiac Abnormalities in Diabetes Mellitus," Am J Cardiol 2002;90:483-487.

Notice of Allowance, mailed Mar. 7, 2007; Related U.S. Appl. No. 11/043,804.

Blendea, Mihaela C., MD, PhD, et al, "Heart Disease in Diabetic Patients," Current Diabetes Reports. 2003;3:223-229.

Eckert, Bodil et al. "Hypoglycaemia leads to an increased QT interval in normal men," Clinical Physiology. 1998;18(6):570-575.

Heller, Simon R, "Abnormalities of the electrocardiogram during hypoglycemia: the cause of the dead in bed syndrome?" Int. J. Clin. Pract. 2002;Suppl. 129:27-32.

Jones, Timothy W. et al., "Mild Hypoglycemia and Impairment of Brain Stem and Cortical Evoked Potentials in Healthy Subjects," Diabetes. 1990;39:1550-1555.

Landstedt-Hallin, L. et al., "Increased QT dispersion during hypoglycaemia in patients with type 2 diabetes mellitus," J Intern Med. 1999;246:299-307.

Malmberg, Klas for the DIGAMI Study Group, "Prospective randomised study of Intensive insulin treatment on long-term survival after acute myocardial infarction in patients with diabetes mellitus", BMJ. May 24, 1997;314:1512-1515.

Robinson, R.T.C.E. et al. "Changes in cardiac repolarization during clinical episodes of nocturnal hypoglycaemia in adults with type 1 diabetes," Diabetologia. 2004;47:312-315.

Peterson, Karl-Georg et al., "Regulation of Serum Potassium During Insulin-Induced Hypoglycemia," Diabetes. Jul. 1982;31:615-617.

Yanowitz, Frank G. MD, Prof. of Medicine, Univ. of Utah School of Medicine, "Lesson X. ST Segment Abnormalities," The Alan E. Lindsay—ECG Learning Center—In Cyberspace, 5 pages.

Steinhaus, Bruce M. et al., "The Information Content of the Cardiac Electrogram at the Stimulus Site," Annual International Conference of the IEEE Engineering in Medicine and Biology Society. 1990;12(2):0607-0609.

Markel, A., Hypoglycaemia-induced ischaemic ECG Changes, Press. Med. 1994;23(2):78-9—Abstract.

First Office Action, mailed Jan. 10, 2007: Related U.S. Appl. No. 11/043,780.

Notice of Allowance, mailed May 9, 2007: Related U.S. Appl. No. 11/043,780.

NonFinal Office Action, mailed Jan. 23, 2008—Related U.S. Appl. No. 11/043,612.

NonFinal Office Action, mailed Jul. 14, 2008—Related U.S. Appl. No. 11/043,612.

NonFinal Office Action, mailed Mar. 25, 2008—Related U.S. Appl. No. 11/117,624.

NonFinal Office Action, mailed Jun. 12, 2008—Related U.S. Appl. No. 11/117,624.

NonFinal Office Action, mailed Sep. 10, 2008—Related U.S. Appl. No. 11/127,370.

* cited by examiner

SYSTEM AND METHOD FOR DETECTING HYPOGLYCEMIA USING AN IMPLANTABLE MEDICAL DEVICE BASED ON PRE-SYMPTOMATIC PHYSIOLOGICAL RESPONSES

CROSS-REFERENCE TO RELATED APPLICATIONS

This application is related to U.S. patent applications:
1) Ser. No. 11/043,780, filed Jan. 25, 2005, titled "System and Method for Distinguishing Among Ischemia, Hypoglycemia and Hyperglycemia Using an Implantable Medical Device", now U.S. Pat. No. 7,272,436;
2) Ser. No. 11/740,175, filed Apr. 25, 2005, titled "System and Method for Efficiently Distinguishing Among Cardiac Ischemia, Hypoglycemia and Hyperglycemia Using an Implantable Medical Device and an External System", now U.S. Pat. No. 7,756,572; and
3) Ser. No. 11/117,624, filed Apr. 27, 2005, titled "System and Method for Detecting Hypoglycemia Based on a Paced Depolarization Integral Using an Implantable Medical Device", now U.S. Pat. No. 7,590,443.

FIELD OF THE INVENTION

The invention generally relates to implantable medical devices such as pacemakers and implantable cardioverter/defibrillators (ICDs) and, in particular, to techniques for detecting hypoglycemia using such devices.

BACKGROUND OF THE INVENTION

Hypoglycemia (i.e. abnormally low blood glucose levels) is believed to be the cause of death in about three percent of insulin-treated diabetic patients. The putative mechanism for death due to hypoglycemia is a hypoglycemia-induced prolongation of the QT interval of the intracardiac electrogram (IEGM), which increases the risk of malignant ventricular tachycardia. See, for example, Eckert et al., "Hypoglycemia Leads to an Increased QT Interval in Normal Men," Clinical Physiology. 1998; 18(6):570-575, and Heller, "Abnormalities of the Electrocardiogram during Hypoglycaemia: The Cause of the Dead in Bed Syndrome," Int. J. Clin. Pract. 2002; Suppl. 129:27-32. Note that the QT interval represents the portion of the IEGM between the beginning of ventricular depolarization and the end of ventricular repolarization. Ventricular depolarization is manifest within the IEGM as a QRS complex (sometimes also referred to as an R-wave.) The QRS complex usually follows an atrial depolarization (also referred to as a P-wave.) Ventricular repolarization is manifest within the IEGM as a T-wave. Note also that the terms P-wave, R-wave and T-wave are also commonly used to refer to features of surface electrocardiograms (ECGs). Herein, the terms refer to the corresponding internal signal components.

In adults, if not treated properly, severe hypoglycemia may result in coma and irreversible brain damage. See, Jones et al., "Mild Hypoglycemia and Impairment of Brain Stem and Cortical Evoked Potentials In Healthy Subjects," DIABETES 1990; 39:1550-1555. Even in cases where hypoglycemia does not cause severe consequences, it is often the limiting factor in achieving effective glycemic control in patients with diabetes, particular insulin-depended diabetics. In this regard, patients sometimes refrain from taking prescribed dosages of insulin for fear that the insulin might trigger an episode of hypoglycemia, which can be quite unpleasant. Failure to take the prescribed insulin prevents the patient from maintaining glycemic levels within a healthy range, thus often leading to additional health problems. Hypoglycemia is also a serious and frequent problem in patients suffering hyperinsulinism, wherein the body generates too much insulin, thereby triggering episodes of hypoglycemia even if an otherwise sufficient amount of sugar or other glucose-generating substances are ingested.

In view of the adverse consequences of hypoglycemia, particularly within insulin-dependent diabetic patients or hyperinsulinism patients, it is highly desirable to provide techniques for detecting hypoglycemia within such patients and automatically delivering appropriate therapy or warning signals. It is known that hypoglycemia can be detected based on observation of changes in the QT interval observed within an ECG, as well as based on observation of dispersion of QT intervals within the ECG (based on studies involving experimental hypoglycemia within adults with type 1 diabetes, i.e. diabetes wherein the body does not make insulin or at least doe not make enough insulin.) Studies in diabetics have also shown that hypoglycemia can be detected based on the observation of a significant lengthening of the QTc interval occurring during spontaneous nocturnal hypoglycemia. See, Robinson et al., "Changes In Cardiac Repolarization During Clinical Episodes Of Nocturnal Hypoglycaemia In Adults With Type 1 Diabetes" Diabetologia 2004; 47:312-5. The QTc interval is an adjusted version of the QT interval that has been corrected to a heart rate of 60 beats per minute (bpm). See, also, U.S. Pat. No. 6,572,542 to Houben, et al., entitled "System and Method for Monitoring and Controlling the Glycemic State of a Patient," which describes a technique exploiting a combination of ECG signals and electroencephalogram (EEG) for the detection of hypoglycemia.

Accordingly, various techniques have been developed for detecting hypoglycemia based on ECG signals. However, it is desirable to provide effective techniques for detecting hypoglycemia based on IEGM signals so that detection may be performed by an implantable medical device without requiring surface electrodes. In particular, it is desirable to provide techniques for detecting hypoglycemia (or for detecting blood glucose levels so that hypoglycemia may be detected therefrom) for use with pacemakers or ICDs, as many patients at risk of hypoglycemia are also candidates for pacemakers and/or ICDs and such devices routinely detect the IEGM for use in pacing the heart and detecting arrhythmias One effective technique for detecting blood glucose levels based on IEGM signals sensed by an implantable medical device is set forth in U.S. Patent Application Serial Number 2004/0077962 of Kroll, published Apr. 22, 2004, entitled "System and Method for Monitoring Blood Glucose Levels Using an Implantable Medical Device." Briefly, with the technique of Kroll, blood glucose levels are determined by an implantable device based on IEGM signals by detecting and examining a combination of T-wave amplitude fraction and QTc interval. The technique may also be used to detect hypoglycemia based on changes in blood glucose levels. Another effective technique for use with implantable devices is set forth in U.S. Patent Application 2006/0167517, of Gill et al., filed Jan. 25, 2005, entitled "System and Method for Distinguishing among Cardiac Ischemia, Hypoglycemia and Hyperglycemia using an Implantable Medical Device." Briefly, techniques are described therein for detecting and distinguishing ischemia, hypoglycemia and hyperglycemia based on IEGM signals. Hypoglycemia is detected based on a change in ST segment elevation along with a lengthening of either the interval between the QRS complex and the peak of the T-wave (QTmax) or the interval between the QRS complex and the end of the T-wave (QTend). By exploiting QTmax and QTend in combination with ST segment elevation, changes in ST segment elevation caused by hypoglycemia can be properly distinguished from changes caused by ischemia or hyperglycemia.

See, also, U.S. Patent Application 2006/0167518, entitled "System and Method for Distinguishing among Cardiac Ischemia, Hypoglycemia and Hyperglycemia using an Implantable Medical Device" and 2006/0167519, also entitled "System and Method for Distinguishing Among Cardiac Ischemia, Hypoglycemia and Hyperglycemia Using an Implantable Medical Device," both to Gill et al., and Ser. No. 11/740,175, filed Apr. 25, 2007, entitled "System and Method for Efficiently Distinguishing among Cardiac Ischemia, Hypoglycemia and Hyperglycemia Using an Implantable Medical Device and an External System," to Fard et al. Still further, see hypoglycemia detection techniques discussed in: U.S. Patent Application 2006/0167365, of Bharmi, filed May 11, 2005, entitled "System and Method for Distinguishing Between Hypoglycemia and Hyperglycemia using an Implantable Medical Device"; U.S. Patent Application 2006/0247685 also of Bharmi, filed Apr. 27, 2005, entitled "System and Method for Detecting Hypoglycemia Based on a Paced Depolarization Integral Using an Implantable Medical Device"; and U.S. patent application Ser. No. 11/757,796, filed Jun. 4, 2007, of Boileau et al., entitled "System and Method for Adaptively Adjusting Cardiac Ischemia Detection Thresholds and Other Detection Thresholds used by an Implantable Medical Device."

Although the techniques of the aforementioned patent applications are effective, it would be desirable to provide still other techniques for detecting hypoglycemia using an implantable medical device and it is to that end that aspects of the present invention are directed. In particular, it is desirable to provide techniques for detecting pre-symptomatic hypoglycemia, i.e. before symptoms are manifest, so as to warn the patient, and other aspects of the invention are directed to that end. In this regard, patients may only become truly symptomatic well after blood glucose levels have dropped into the hypoglycemic range. In the absence of pre-symptomatic warnings, the patients would have to depend on symptoms to know that a hypoglycemic event is ongoing, which thus delays any needed medical attention. Relying on symptoms is even more problematic in patients who have had earlier episodes of hypoglycemia, as such patients can become desensitized to the symptoms of hypoglycemia. Also, the majority of hypoglycemic events may occur while the patient is sleeping when the symptoms are minimal or unnoticeable. Hence, a technique providing for pre-symptomatic detection of hypoglycemia would be particularly advantageous.

SUMMARY OF THE INVENTION

In an exemplary embodiment, a method is provided for use with an implantable medical device such as a pacemaker or ICD for detecting hypoglycemia within a patient in which the device is implanted. Briefly, an electrical cardiac signal such as an IEGM is sensed. Values representative of a pre-symptomatic physiologic response to a hypoglycemic event are derived from the cardiac signal. Then, hypoglycemia is detected based on the values representative of the pre-symptomatic physiologic response. In one example, both temporal morphological parameters and spectral parameters affected by pre-symptomatic hypoglycemia are derived from the cardiac signal. Hypoglycemia is then detected based on a combination of the temporal parameters and the spectral parameters. In any case, by detecting hypoglycemia based on parameters affected by pre-symptomatic hypoglycemia, suitable warnings can be generated and therapies initiated before the condition becomes symptomatic.

Temporal morphological parameters affected by pre-symptomatic hypoglycemia include, e.g., T-wave parameters; P-wave parameters; QRS parameters; far-field waveform morphological parameters; QT dynamics parameters; heart rate parameters; or paced depolarization integrals (PDIs). Other temporal parameters affected by pre-symptomatic hypoglycemia include respiratory parameters such as respiration rate and respiration depth. The various temporal parameters may be analyzed, depending upon the embodiment, to derive one or more of the mean, standard deviation and variance of the values or to derive parameters representative of changes in time within the values (i.e. trends). Spectral parameters affected by pre-symptomatic hypoglycemia include spectral power values derived from the aforementioned temporal parameters or from the cardiac signal as a whole. Spectral power may be derived, e.g., using a fast Fourier transform (FFT). The various spectral parameters may be analyzed, depending upon the embodiment, to derive mean spectral power or to determine a ratio of relatively low frequency components to relatively high frequency components.

To detect hypoglycemia, the pacemaker or ICD then applies the various temporal and spectral parameters derived from the cardiac signal to decision logic within the device, which then detects hypoglycemia within the patient by applying suitable threshold values to the various parameters or by employing a linear discriminator or the like. Preferably, before the temporal and spectral parameters are applied to the decision logic, data outliers (i.e. anomalous data points) within the parameters are detected and eliminated. Also, the cardiac signal data is preferably normalized based on patient activity level, body position and cardiac rhythm type (e.g., whether the patient's heartbeats are predominantly paced or sensed). Patient gender and information stored within the device pertaining to patient history may be exploited by the decision logic to improve the specificity of the decision logic. If the device is equipped to directly detect blood glucose levels, the device can detect pre-symptomatic hypoglycemia based on both the aforementioned parameters along with trends in the blood glucose measurements. For example, slight decreases in blood glucose levels may be used to confirm pre-symptomatic hypoglycemia detection made based on the temporal and spectral cardiac signal parameters, or vice versa. Still further, other conditions associated with hypoglycemia can be detected and exploited by the decision logic, such as episodes of tachycardia. Also, if so equipped, the implantable device may input information entered by the patient via an external device that is relevant to the detection of hypoglycemia such as information pertaining to one or more of excessive perspiration, tremors (i.e. shakiness), skin pallor, anxiety, hunger, warmth, light-headedness, weakness, headache, confusion, lack of coordination, and speech difficulty.

Upon detecting hypoglycemia, appropriate warning signals are generated, which may include perceptible signals applied to subcutaneous tissue or short range telemetry warning signals transmitted to a device external to the patient, such as a bedside monitor. In one example, once a subcutaneous warning signal is perceived, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal. Upon confirmation of the warning, the patient then takes appropriate actions, such as ingesting sugar pills suitable for increasing blood glucose levels in response to hypoglycemia. If the patient has an external blood glucose monitor, the patient may confirm the detection of hypoglycemia using that device before taking further action.

Certain therapies automatically provided by the implantable device may also be initiated or modified in response to hypoglycemia. If the patient is an insulin-dependent diabetic and the implantable device is equipped with a drug pump capable of delivering insulin directly into the bloodstream, insulin delivery by the pump is automatically suspended during hypoglycemia until blood glucose levels return to acceptable levels. If the patient suffers hyperinsulinism and if the drug pump is equipped to deliver medications appropriate to hyperinsulinism, delivery of such medications is titrated in response to the glycemic state. In addition, if the device is an ICD, it may be controlled to begin charging defibrillation capacitors upon detection of hypoglycemia so as to permit prompt delivery of a defibrillation shock, which may be needed if hypoglycemia triggers VF due to a prolongation of the QT intervals. Additionally, or in the alternative, data representative of pre-symptomatic hypoglycemia or trend information pertaining to the temporal or spectral-based parameters used to detect hypoglycemia are stored for subsequent physician review, such as date/time and duration of the episode, the individual temporal and spectral values detected, trends found therein, and any therapies automatically delivered. Trend information is especially helpful as it allows the patient and physician to develop and implement strategies for achieving better glycemic control within the patient.

Also, preferably, trend information is used to detect episodes of hypoglycemia as early as possible so that warning signals may be generated to alert the patient to take appropriate action to prevent the episode from occurring. For example, if the trend data indicates that the patient frequently has episodes of hypoglycemia early in the morning and the aforementioned temporal and spectral parameters are found to be significantly increasing early on a particular morning, then a warning signal is issued notifying the patient that an episode of hypoglycemia is likely.

Hence, improved techniques are provided for reliably detecting hypoglycemia, particularly pre-symptomatic hypoglycemia. The techniques are preferably performed by the implanted medical device itself so as to provide prompt warnings when needed. Alternatively, the techniques may be performed by external devices, such as bedside monitors or the like, based on IEGM signals detected by an implanted device then transmitted to the external device.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable System

Figure 1:
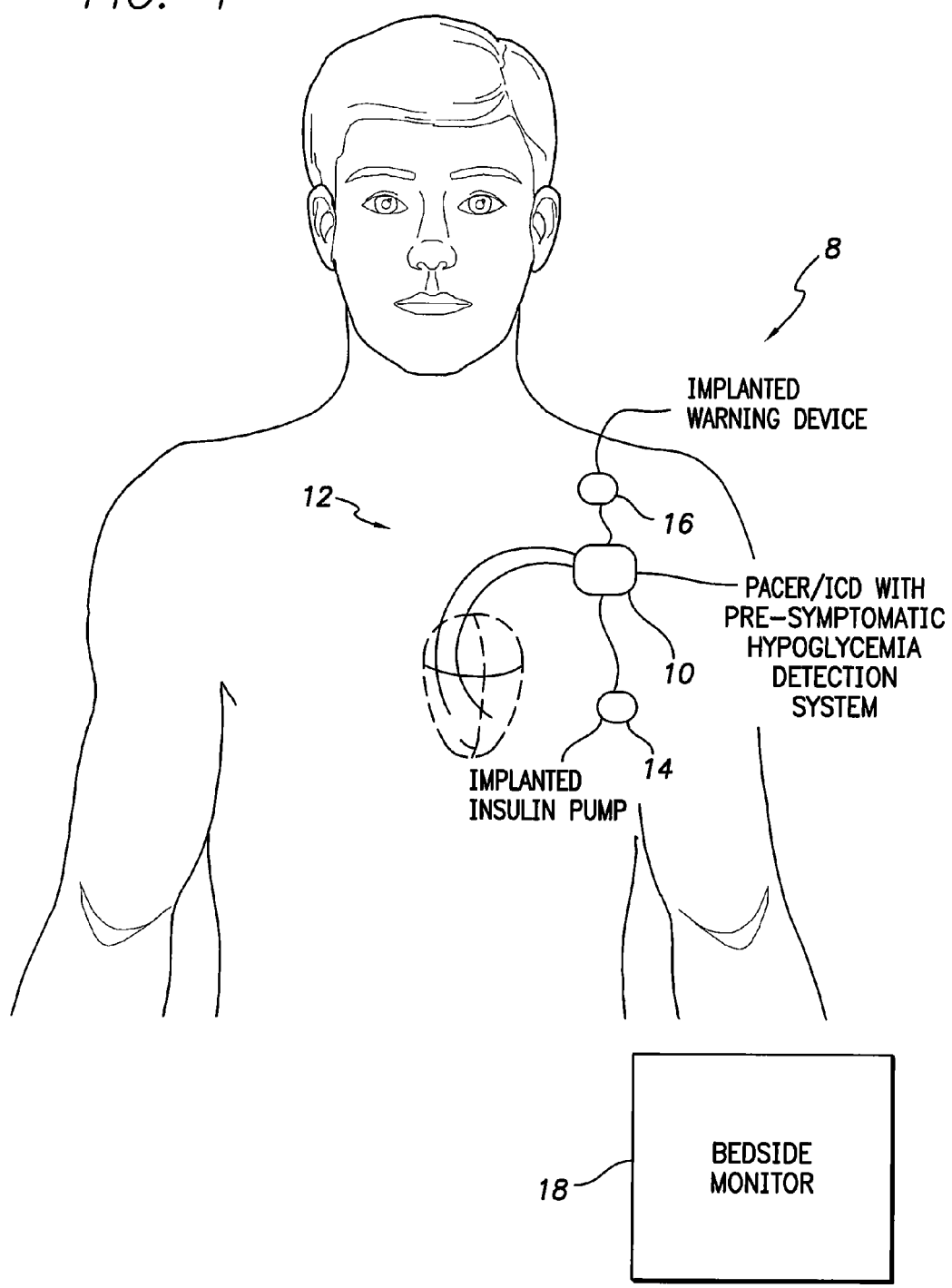
FIG. 1 illustrates pertinent components of an implantable medical system with a pre-symptomatic hypoglycemia detection system.
Figure 7:
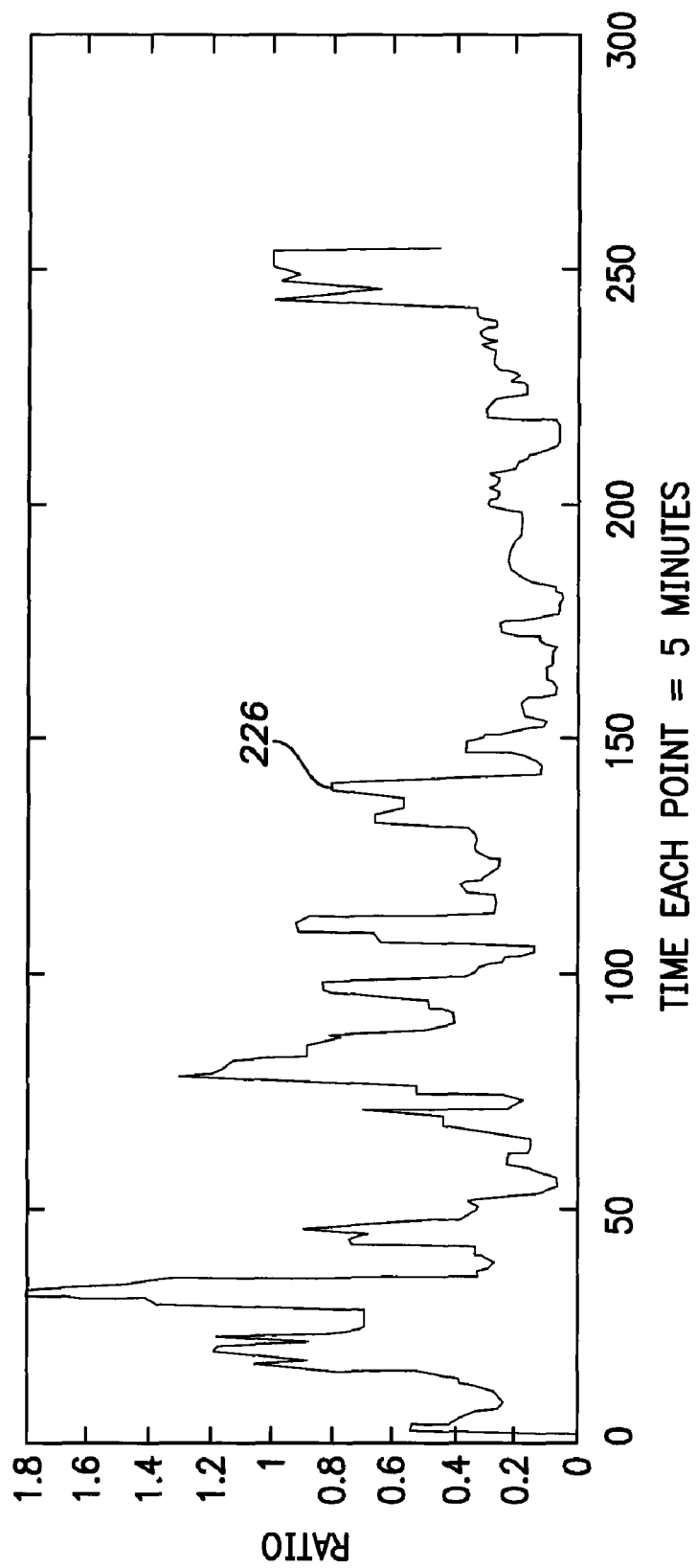
FIG. 7 is a graph illustrating changes over a twenty-one hour period in the ratio of LF to HF components of T-wave integrals for a test subject without hypoglycemic events, which particularly illustrates that the ratio of LF to HF remains low in the absence of hypoglycemia even during periods of patient activity.
Figure 8:
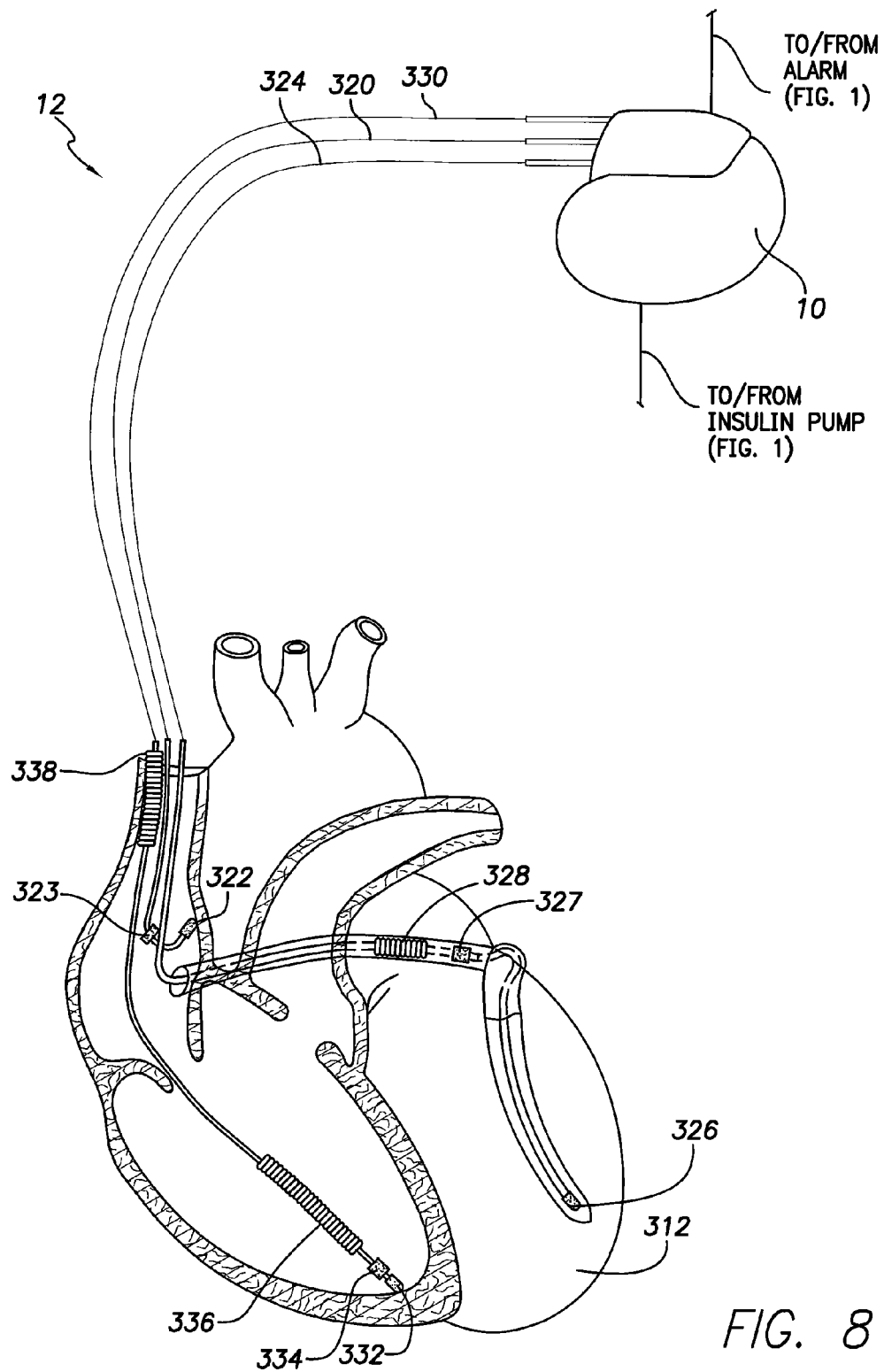
FIG. 8 is a simplified, partly cutaway view, illustrating the pacer/ICD of FIG. 1 along with a more complete set of leads implanted into the heart of the patient.

FIG. 1 illustrates an implantable medical system 8 having a pacer/ICD 10 capable of detecting pre-symptomatic as well as symptomatic hypoglycemia events based on electrical cardiac signals sensed within the patient in which the pacer/ICD is implanted. To sense the electrical cardiac signals, the pacer/ICD uses a set of cardiac pacing/sensing leads 12 implanted on or within the heart of the patient from which one or more IEGM signals is derived. In FIG. 1, only two pacing leads are shown. A more complete set of pacing leads is shown in FIG. 8, discussed below. Exemplary techniques used by the pacer/ICD to analyze the IEGM signals to detect hypoglycemia (particularly pre-symptomatic hypoglycemia) are explained in detail with reference to FIGS. 2-7.

If pre-symptomatic or symptomatic hypoglycemia is detected, appropriate therapy may be automatically delivered by the implantable system under the control of the pacer/ICD. As can be appreciated, by detecting hypoglycemia events before symptoms are noticeable by the patient, the pacer/ICD can promptly initiate therapy to address the event so as to prevent the event from then becoming symptomatic. For example, for insulin dependent patients, the dosage of insulin delivered to the patient via an implanted insulin pump 14 (if so equipped) may be titrated in response to detection of pre-symptomatic hypoglycemia in an effort to prevent the episode from becoming symptomatic. Techniques for controlling delivery of therapy in response to hypoglycemia are set forth in the patent application of Kroll cited above (2004/0077962). Information regarding implantable insulin pumps may be found in U.S. Pat. No. 4,731,051 to Fischell and in U.S. Pat. No. 4,947,845 to Davis. Warning signals may additionally, or alternatively, be generated to alert the patient. For example, if pre-symptomatic hypoglycemia is detected, the patient may be warned by application of an internal perceptible "tickle" notification signal using an implanted warning device 16. The patient can then take sugar pills or other appropriate foods or medications to alleviate the hypoglycemia. "Tickle" warning devices are discussed in U.S. Pat. No. 5,328,460 to Lord, et al., entitled "Implantable Medication Infusion Pump Including Self-Contained Acoustic Fault Detection Apparatus." If the device is configured to generate warning signals for other abnormal conditions, such as hyperglycemia or ischemia, the device preferably employs different notification signal frequencies for the different warnings so that the patient can properly distinguish between different warnings.

In addition, warning signals may be transmitted using a short-range telemetry system to a bedside monitor 18 or to a handheld warning device (not separately shown) using techniques described within U.S. patent application Ser. No. 10/603,429, entitled "System And Method For Detecting Cardiac Ischemia Using an Implantable Medical Device," of Wang et al. The bedside monitor or handheld warning device provides audible or visual alarm signals to alert the patient, as well as textual or graphic displays. The bedside monitor or handheld warning device thereby provides confirmation of the warning to the patient, who may be otherwise uncertain as to the reason for the internally generated tickle warning signal. The bedside monitor or handheld warning device can also provide specific instructions to the patient. In some implementations, the handheld warning device may be equipped to allow the patient to input information pertaining to his or her current health status to help confirm a diagnosis of hypoglycemia, such as information pertaining to excessive perspiration, tremors, skin pallor, etc. Note that these confirmatory conditions usually are not noticeable by the patient until the hypoglycemia becomes symptomatic (i.e. these conditions represent possible symptoms of hypoglycemia.) Nevertheless, the information is helpful at least in confirming the presence of hypoglycemia. Also, as will be discussed below, such information may be exploited by decision logic of the pacer/ICD to refine or improve its pre-symptomatic hypoglycemia detection capabilities. Note also that at least some of these confirmatory conditions can also be directly detected by the pacer/ICD using suitable implantable sensors (not separately shown) such as sensors equipped to sense skin surface resistance changes to detect excessive perspiration or motion sensors equipped to sense tremors.

In addition, once pre-symptomatic or symptomatic hypoglycemia has been detected, diagnostic information is generated within the pacer/ICD for transmission to the bedside monitor or for subsequent transmission to an external programmer (not shown in FIG. 1) for review by a physician or other medical professional. The physician may then prescribe any other appropriate therapies to prevent additional episodes of hypoglycemia. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of hypoglycemia, particular if it appears severe. Networking techniques for use with implantable medical systems are set forth, for example, in U.S. Pat. No. 6,249,705 to Snell, entitled "Distributed Network System for Use with Implantable Medical Devices." Note that, in at least some implementations, lower internal detection thresholds may be used to trigger recording of hypoglycemia diagnostics, with higher thresholds used for triggering warnings, and still higher thresholds for triggering automatic delivery of therapy.

Hence, FIG. 1 provides an overview of an implantable system having components for detection pre-symptomatic hypoglycemia and for delivering appropriate therapy or warnings. Systems provided in accordance with the invention need not include all the components shown in FIG. 1. In many cases, for example, the system will include only the pacer/ICD and its leads. Insulin pumps and warning devices are not necessarily implanted. In addition, although internal signal transmission lines are illustrated in FIG. 1 for interconnecting the various implanted components, wireless signal transmission may alternatively be employed. Furthermore, the particular locations, orientations and relative sizes of the implanted components shown in FIG. 1 are merely illustrative and may not necessarily correspond to actual implant locations, orientations or relative sizes.

Hypoglycemia Detection Techniques

Figure 2:
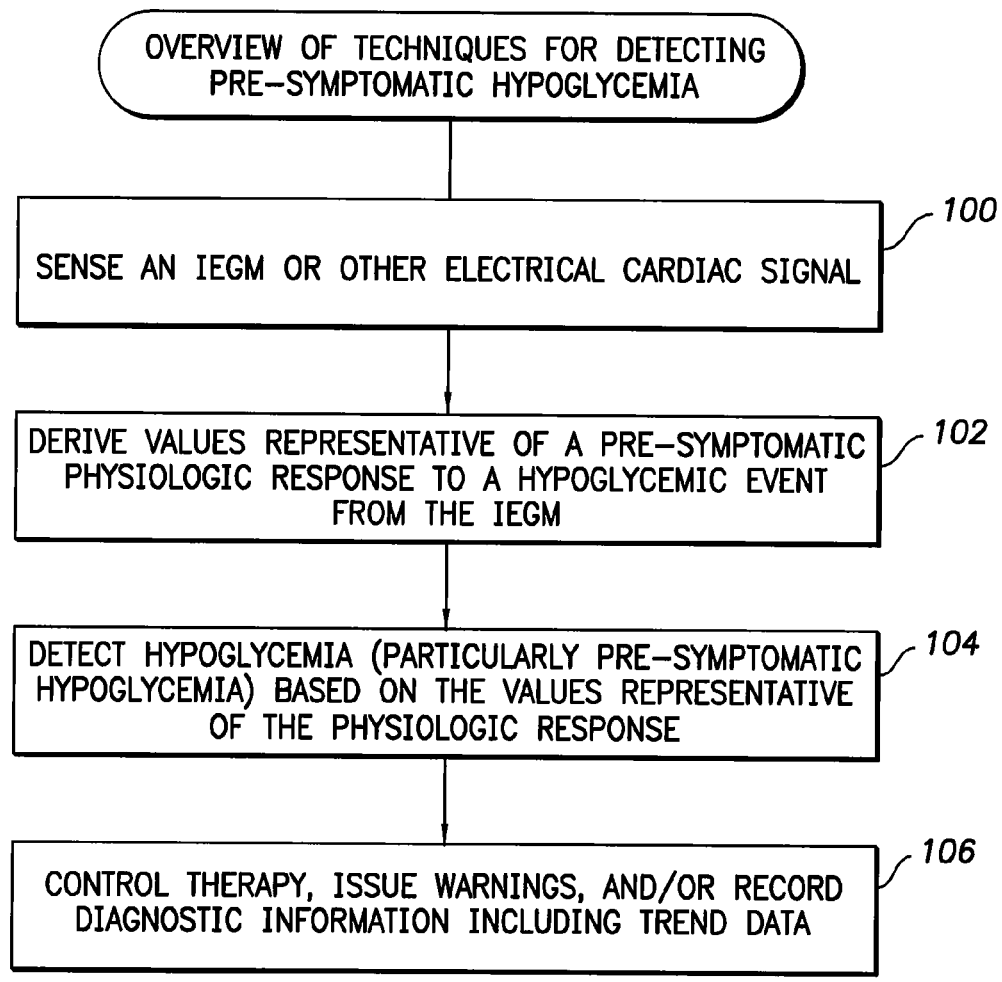
FIG. 2 is a flow diagram providing an overview of the techniques for detecting hypoglycemia that may be exploited by the system of FIG. 1.

FIG. 2 broadly summarizes the hypoglycemia technique performed by the system of FIG. 1, which can detect pre-symptomatic hypoglycemia. Briefly, at step 100, the pacer/ICD senses an IEGM or other electrical cardiac signal and, at step 102, derives values representative of a pre-symptomatic physiologic response to a hypoglycemic event from the cardiac signal, i.e. values representative of changes within patient physiology (particularly cardiac physiology) caused by blood glucose levels beginning to drop below healthy or nominal levels. Examples of suitable values derived at step 102 include both temporal values (i.e. parameters derived from time-varying components of the cardiac signals) and spectral values (i.e. parameters derived from frequency-varying components of the cardiac signals). The particular parameters to be derived from the cardiac signal may vary from patient to patient.

Temporal values representative of the pre-symptomatic physiologic response to a hypoglycemic event within a particular patient may include, e.g., T-wave parameters; P-wave parameters; QRS parameters; far-field waveform morphological parameters (e.g. far-field R-waves observed in the atria); QT dynamics parameters; heart rate parameters; or PDIs, as well as integrals of various morphological parameters such as T-wave integrals. The particular morphological parameters to be measured may include, e.g., various duration-based parameters such as P-wave width, QRS-complex width and T-wave width; various slope-based parameters such as maximum P-wave slope, maximum QRS-complex slope and maximum T-wave slope; various amplitude-based parameters such as peak P-wave amplitude, peak QRS-complex amplitude and peak T-wave amplitude. The QT dynamics parameters to be detected include the above-described QTmax and QTend parameters or other suitable parameters. Heart rate parameters may include atrial and ventricular rates, as well as parameters derived therefrom such as heart rate variability parameters. PDI parameters may include integrals derived from paced events as well as corresponding integrals derived from sensed events.

Still other temporal parameters representative of the pre-symptomatic physiologic response to a hypoglycemic event within a particular patient may include, e.g., respiratory parameters such as respiration rate and respiration depth. Respiration may be obtained from the cardiac signal using techniques described in, e.g., U.S. patent application Ser. No. 11/100,189 of Koh, entitled "System and Method for Detection of Respiration Patterns via Integration of Intracardiac Electrogram Signals." Respiration can also be derived from impedance pulses using otherwise conventional techniques. Spectral parameters that may be representative of the pre-symptomatic physiologic response to a hypoglycemic event within a particular patient may include, e.g., spectral power values derived from the aforementioned temporal parameters or from the cardiac signal as a whole. Spectral power may be calculated using otherwise conventional techniques such as FFTs. The various spectral parameters may be analyzed, depending upon the embodiment, to derive mean spectral power or to determine a ratio of relatively low frequency components to relatively high frequency components.

At step 104, the pacer/ICD then detects hypoglycemia—particularly pre-symptomatic hypoglycemia—based on the values obtained at step 102, i.e. the values representative of the physiologic response within the patient to a hypoglycemic event. Any of a variety of decision techniques may be exploited to render such a determination based on the various values obtained at step 102. Examples are described below wherein linear discriminators or similar devices or procedures are exploited. As can be appreciated, by obtaining and exploiting values representative of the pre-symptomatic response within the patient to dropping blood glucose levels, the pacer/ICD can detect hypoglycemia before it becomes symptomatic. Additionally, or alternatively, the procedure can be used to detect symptomatic hypoglycemia as well. At step 106, the pacer/ICD then controls therapy, issues warnings, and/or records diagnostic information (including trend data), as already discussed. In addition, if the device is an ICD, it may be controlled to begin charging defibrillation capacitors upon detection of hypoglycemia so as to permit prompt delivery of a defibrillation shock, which may be needed if hypoglycemia triggers VF due to a prolongation of the QT intervals.

Figure 3:
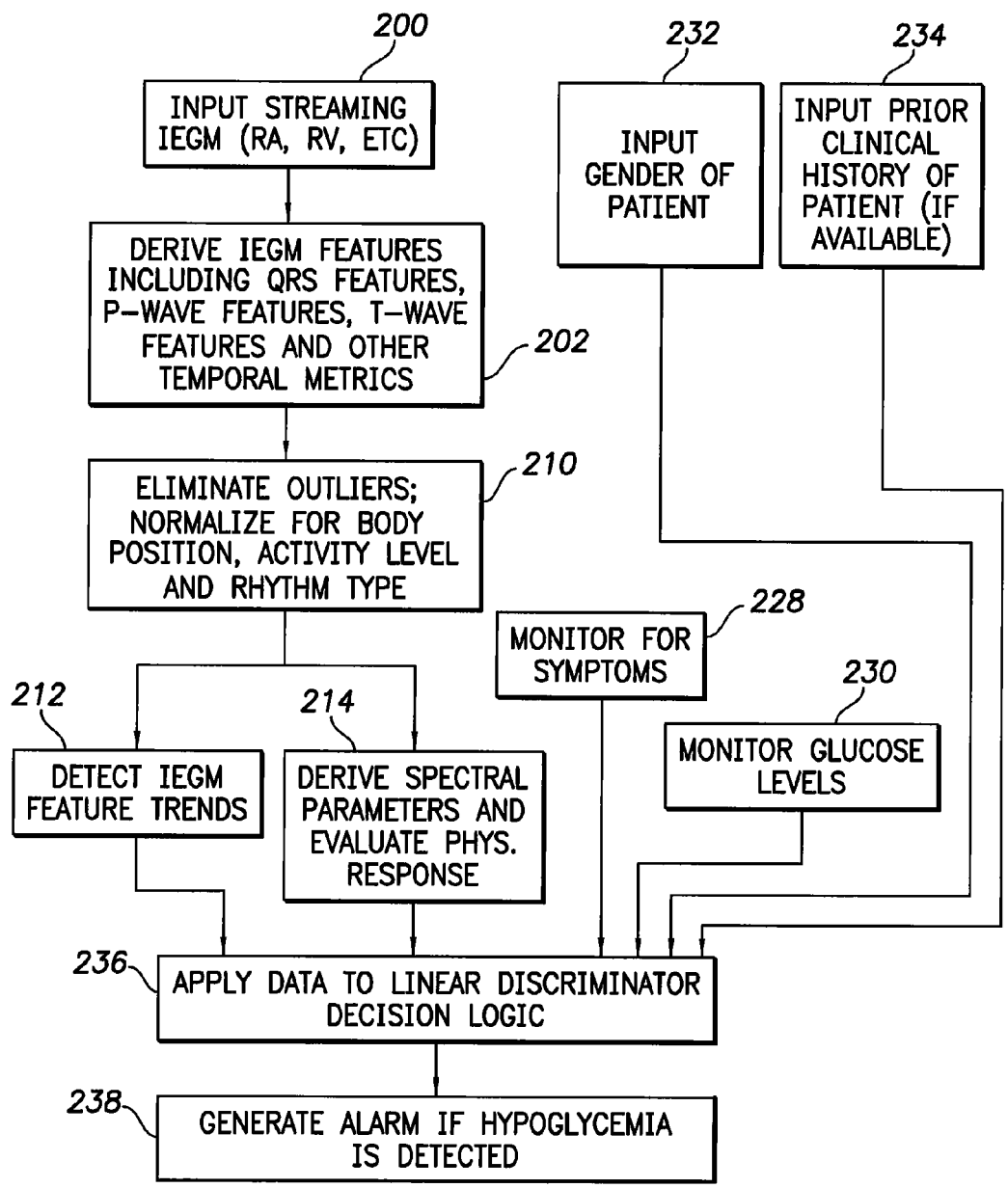
FIG. 3 is a flow diagram illustrating an exemplary implantation of the general technique of FIG. 2, which exploits both temporal and spectral cardiac signal parameters in detecting hypoglycemia.
Figure 4:
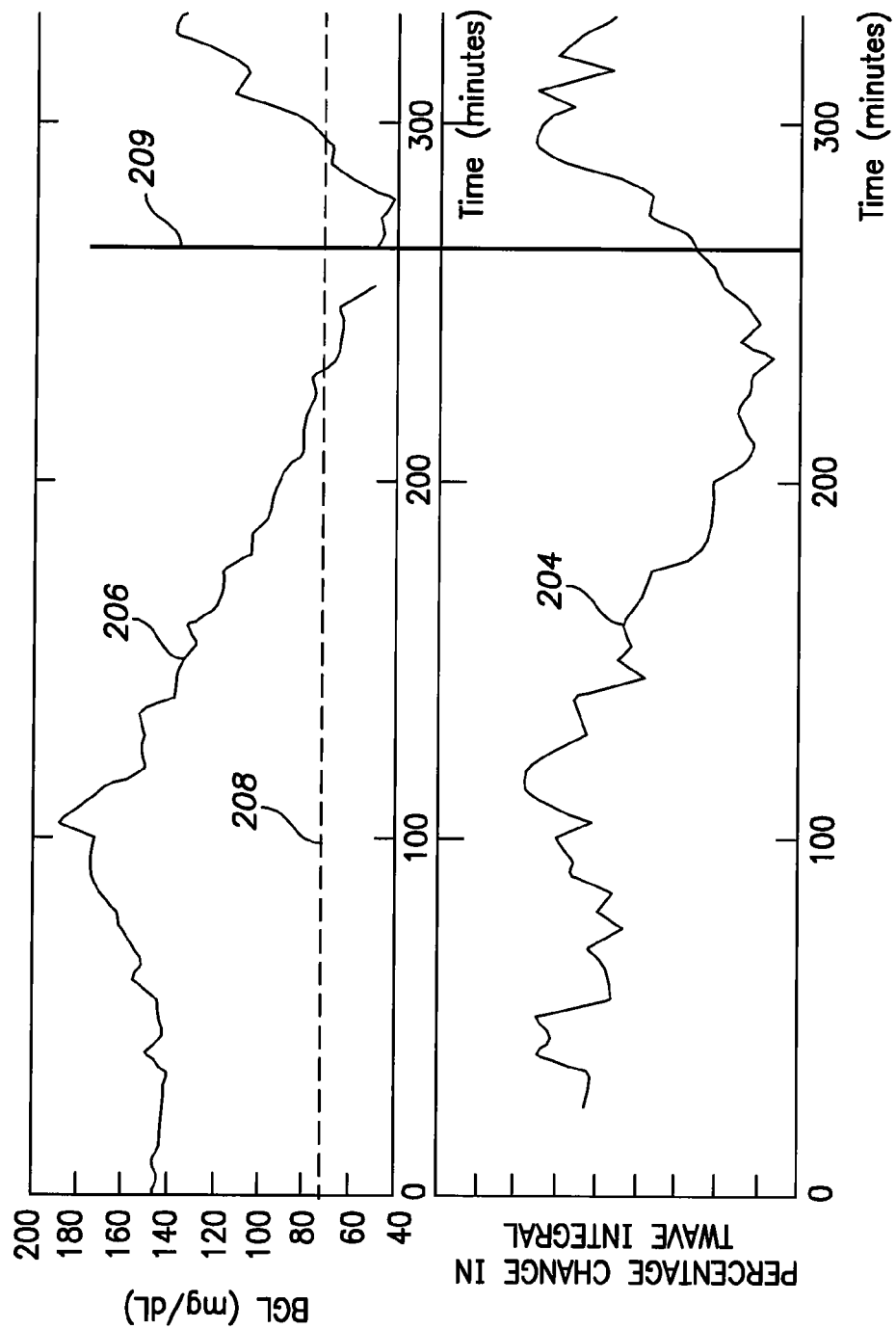
FIG. 4 is a graph illustrating changes over time in blood glucose levels and in T-wave temporal integrals during an episode of hypoglycemia, which may be exploited by the implementation of FIG. 3.

FIGS. 3-7 illustrate an exemplary hypoglycemia detection procedure. At step 200, the pacer/ICD inputs streaming IEGM signals from leads implanted within the heart, such as a right atrial (RA) lead, a right ventricular (RV) lead, etc. At step 202, the pacer/ICD derives IEGM features from the signals that are affected by the pre-symptomatic physiologic response to hypoglycemia including, in this particular example, QRS features, P-wave features, T-wave features and other temporal metrics such as integrals of the various features. In particular, T-wave morphology is known to change during hypoglycemic events. FIG. 4 includes a graph 204 of changes in T-wave integrals over time as blood glucose levels (BGL) drop to hypoglycemic levels within a test subject. More specifically, graph 204 plots the percentage change within the T-wave integral as a function of time over a period of about five hours. That is, the vertical scale of the plot represents the change in T-wave integral relative to a baseline value along an arbitrary scale. Graph 206 shows changes in BGL in mg/dL over the same period of time. BGL was changed within this test subject from a mean of 160 mg/dL to 50 mg/dL over a period of about three hours. T-wave integrals tend to increase within increasing BGL and then decrease with decreasing BGL. A horizontal line indicative of a BGL threshold for hypoglycemia is identified by reference numeral 208. A vertical line 209 indicates the time at which the test subject was first symptomatic of hypoglycemia. As can be seen, the T-wave integrals decrease well in advance of that point. That is, decreases in T-wave integrals are representative of pre-symptomatic hypoglycemia. Accordingly, T-wave integrals may be employed as a metric indicative of pre-symptomatic hypoglycemia. As already explained, various other temporal features derived from the IEGM, besides T-wave integrals, can change with an impending hypoglycemic event such as P-wave morphology metrics, QRS-morphology metrics, far-field morphology metrics, T-wave morphology metrics, QT dynamics, heart rate, respiration rate, respiration depth, etc., and hence these values may be derived as well at step 202 of FIG. 3. The mean, standard-deviation, and variance provide information on the changes in the features over time.

At step 210, the pacer/ICD eliminates outliers within the data obtained at step 202 (i.e. anomalous data points) and also normalizes the data based on body position, activity levels and heath rhythm. Various methods e.g. running average, filters, or percentile-based outlier removal methods can be used to remove outliers from the data and replace the removed data with, e.g., the current running average of the IEGM feature value. Insofar as normalization is concerned, IEGM features can change due to various reasons: body position changes, rhythm type, activity level etc. Body position or posture may be detected using techniques set forth in, e.g., U.S. patent application Ser. No. 10/329,233, of Koh et al., entitled "System and Method for Determining Patient Posture based on 3-D Trajectory Using an Implantable Medical Device," filed Dec. 23, 2002. Methods for correcting for noise introduced by body position changes are set forth in: U.S. patent application Ser. No. 11/623,676, filed Jan. 16, 2007, and in U.S. patent application Ser. No. 11/623,681, filed Jan. 16, 2007. Activity levels may be detected using an activity sensor, such as an accelerometer. The manner by which changes in activity levels or posture can affect IEGM parameters is discussed within the application to Boileau et al., sited above.

The current heart rhythm of the patient may be detected by determining the relative percentages of paced to sensed beats. In one example, if most beats are sensed, the patient's heart rhythm is deemed to be intrinsic (i.e. a sinus rhythm). If most beats are paced, the patient's heart rhythm is instead deemed to be paced. In other examples, the device further distinguishes among four different cardiac rhythms: AR (paced atrial beats/intrinsic ventricular beats); AV (paced atrial beats/paced ventricular beats); PR (intrinsic atrial beats/intrinsic ventricular beats); and PV (intrinsic atrial beats/paced ventricular beats). The manner by which different heart rhythms can affect the features of IEGM signals is discussed within U.S. patent application Ser. No. 11/558,787, filed Nov. 10, 2006, of Bharmi et al., entitled "System and Method for Detecting Physiologic States based on Intracardiac Electrogram Signals while Distinguishing Cardiac Rhythm Types." In particular, that application describes a system and method for detecting respiration based on IEGM signals while distinguishing cardiac rhythm types, and illustrates how the effect of rhythm changes can be eliminated to ensure that rhythm changes do no affect co-morbidity detection techniques.

At step 212, the pacer/ICD then examines the filtered and normalized IEGM data to detect trends within the data, particularly significant changes over time. In the example of FIG. 4, the pacer/ICD would thereby detect the trend in decreasing T-wave integral values. Preferably, these trends are quantified so that information pertaining to the trends can then be input to a linear discriminator or other decision logic devices or circuits. In this regard, since many conditions and events can change the IEGM, time trending is used for each feature because blood glucose levels change in a consistent manner. BGL changes at a rate of less than ±1 mg/dl/min 90% of the time, less than ±2 mg/dl/min 95% of the time, and less than ±3 mg/dl/min 99% of the time. Hence, the minimum amount of time it would take to go from euglycemic (~100 mg/dl) to hypoglycemic (~65 md/gl) is about 12 minutes with the average time to change from euglycemic to hypoglycemic greater than 40 minutes. This differs significantly from other conditions/events that change the IEGM such as: apnea (<2 minutes), ischemia (<10 minutes), acute decompensated of heart failure (>1 day), etc. Hence, by incorporating the time trending of the features to match the glucose rate of change, the pacer/ICD can increase the specificity of the detection procedure.

Figure 5:
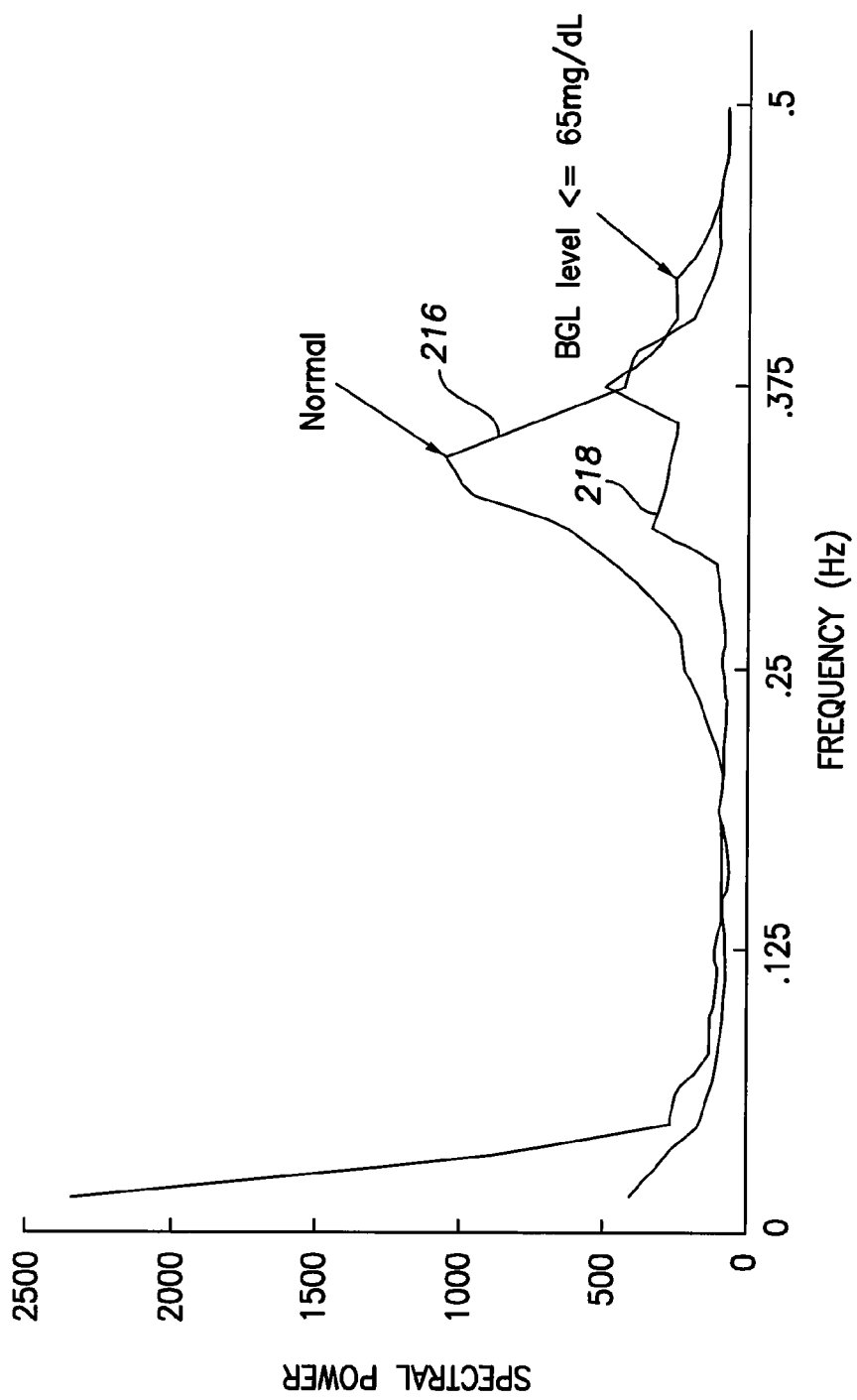
FIG. 5 is a graph illustrating differences in the spectral power of T-waves between hypoglycemia and normal blood glucose conditions, which also may be exploited by the implementation of FIG. 3.
Figure 6:
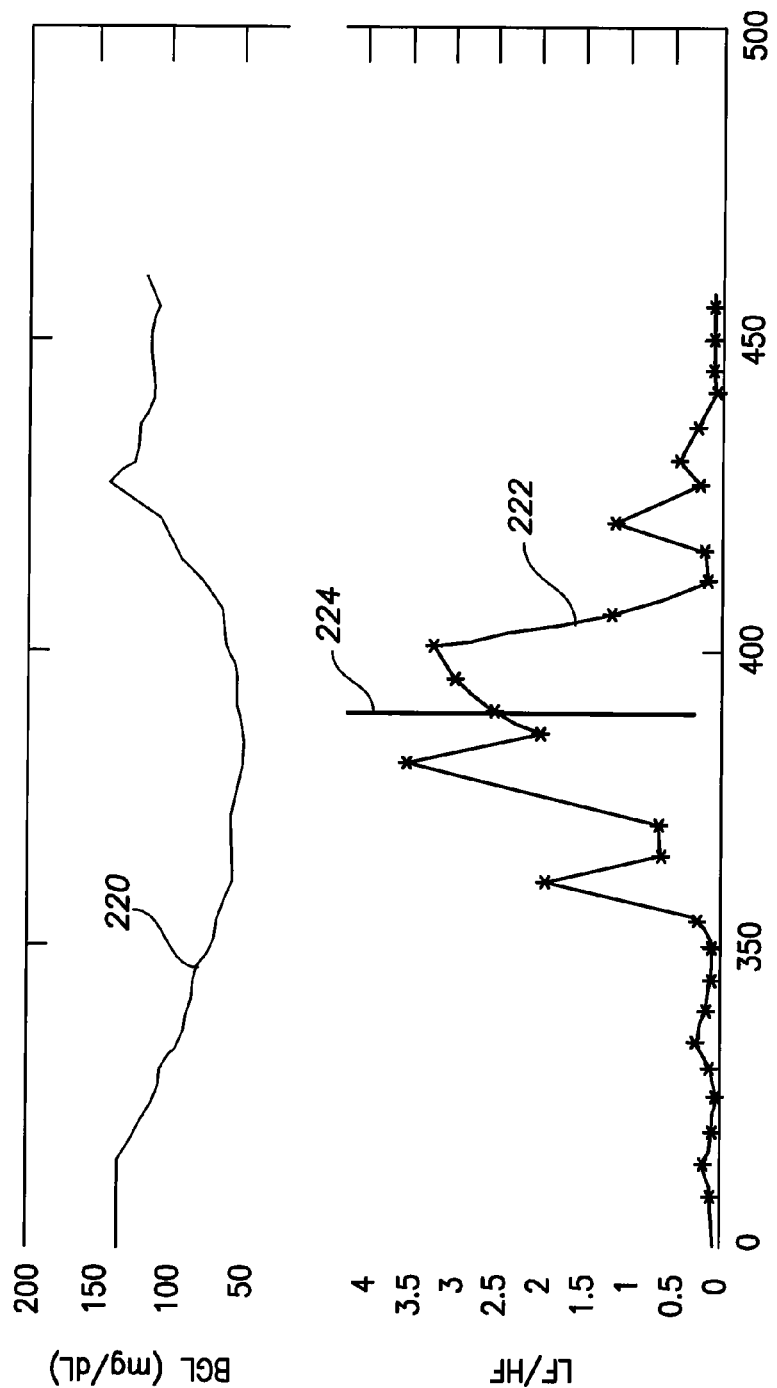
FIG. 6 is a graph illustrating changes over time in blood glucose levels and in a ratio of low frequency (LF) to high frequency (HF) components of T-wave integrals, which also may be exploited by the implementation of FIG. 3.

Returning to FIG. 3, at step 214, the pacer/ICD derives frequency domain components (i.e. spectral components) of all or some of the temporal features originally derived at step 202 and evaluates the physiological response to a possible episode of hypoglycemia. As noted, a FFT may be used to convert temporal parameters to spectral parameters. FIG. 5 illustrates differences in frequency components of T-wave integrals between normal conditions 216 and hypoglycemic conditions 218. In each case, T-wave integrals were first calculated based on IEGM signals derived from heartbeats obtained over a period of time, thus yielding time-varying T-wave integral data. The data set was divided into two sets: Normal, i.e. samples of T-wave integrals when BGL was above 65 mg/dL, and Hypoglycemic, i.e. samples of T-wave integrals when the BGL level was less than 65 mg/dL. A FFT was applied to the T-wave integral data of each data set every five minutes using the T-wave integrals obtained from the latest 128 heartbeats of that data set so as to derive spectral power. The mean spectral power for the T-wave integrals with normal BGL is represented by graph 216; whereas the mean spectral power for the T-wave integrals with hypoglycemic BGL is represented by graph 218. As can be seen, in each case spectral power peaks in the range of 0.25 to 0.5 Hz. However, the amplitude of the peak of the spectral power for Normal BGL T-wave integrals is considerably higher than that of Hypoglycemic BGL T-wave integrals. Also, the peak of the spectral power of the Hypoglycemic BGL T-wave integrals is somewhat higher in frequency. Hence, both peak frequency and peak amplitude is, in this case, indicative of BGL. The peak amplitude and/or peak frequency (or other suitable quantified values of the T-wave spectral power data) is then input to the linear discriminator.

Other types of spectral power data derived from other IEGM parameters may likewise be quantified for input to the linear discriminator. As another example, a ratio of low frequency (LF) to high frequency (HF) portions of the spectral power may be calculated and applied to the linear discriminator. This is illustrated by way of FIG. 6, which shows BGL levels 220 changing over time, along with an LF/HF ratio 222, likewise changing over time. As can be noted from the BGL levels, a period of hypoglycemia occurred, reaching a peak between 350 to 400 minutes into the recorded data. The LF/HF ratios were calculated by calculating T-wave integrals then applying a FFT to the latest T-wave integral values to convert to obtain frequency-domain power spectra. Each power spectra was subdivided into LF and HF portions using a suitable cutoff frequency. Then the ratio of LF to HF was calculated. This procedure was repeated at uniform intervals of about once every five minutes to yield the time-varying plot 222 of LF/HF. As can be seen, the LF/HF ratio peaked during the episodes of hypoglycemia. That is, LF/HF had a baseline of less than 0.5 but increased to above 2.5 during the hypoglycemic event. Again, a vertical line indicates when the test subject became symptomatic. Most notably, the LF/HF values increased significantly before the patient became symptomatic, thus indicating the desirability of using LF/HF ratios in the detection of pre-symptomatic hypoglycemia. FIG. 7 illustrates LF/HF ratios obtained over a period of about twenty-one hours for the same test subject (normalized for rhythm types but not activity), during which no hypoglycemic events occurred. As can be seen from LF/HF graph 226, even at its peak, the LF/HF ratio remained below 2.0, and thus well below the ratio of 2.5 obtained during a hypoglycemic event, further indicating the efficacy of using LF/HF ratios in hypoglycemia detection. The LF/HF ratio, thus, represents another type of data that may be applied to the linear discriminator or other logic circuit.

Returning to FIG. 3, at step 228, the pacer/ICD also monitors for symptoms, if any, that have already occurred due to hypoglycemia. As already explained, although the overall technique is directed to detecting pre-symptomatic hypoglycemia, it is also appropriate to monitor for any symptoms of hypoglycemia that have been manifest, either by using implantable sensors or by receiving patient input via a handheld communication device or the like. Symptom information that may be input via an external device includes information pertaining to excessive perspiration, tremors, skin pallor, anxiety, hunger, warmth, light-headedness, weakness, headache, confusion, lack of coordination, and speech difficulty. Also, the pacer/ICD can also directly monitor for episodes of tachycardia or abnormal respiration that might be symptomatic of hypoglycemia. If provided with suitable sensors, the pacer/ICD can also directly detect tremors and excessive perspiration. Otherwise conventional numerical techniques may be used to quantify this information for input to a linear discriminator or other logic device. At step 230, the pacer/ICD monitors blood glucose levels, if so equipped, for input to the linear discriminator. Otherwise conventional glucose detectors may be used. As already explained, information pertaining to actual blood glucose levels can be used in combination with the IEGM-derived parameters and other information to detect hypoglycemia.

Additionally, as shown, the gender of the patient and any pertinent patient history may be input, at steps 232 and 234, and applied to the linear discriminator. This data may be retrieved from memory. Insofar as gender is concerned, it is known that the response to hypoglycemia differs by gender. Hence, gender information aids in hypoglycemia detection. Insofar as patient history is concerned, such information is initially input by the patient or a clinician and quantified for processing by the linear discriminator. In one example, if the patient history indicates previous episodes of hypoglycemia, such is indicated by way of a suitable numerical value whereas, if the patient has no history of hypoglycemia, such is indicated by a different numerical value. Likewise, information pertaining to other medical conditions diagnosed within the patient may be quantified, such as any prior episodes of ischemia, apneas, etc. As can be appreciated, a wide variety of patient history data that might be pertinent to the detection of pre-symptomatic hypoglycemia may be quantified for input to the linear discriminator or other logic circuit.

At step 238, all of the data collected and processed at steps 212, 214, 216, 230, 232 and 234 is then applied to a linear discriminator trained to recognize pre-symptomatic hypoglycemia based on the data or to any other suitable logic decision circuit, device or software program. For example, threshold based methods/discriminant analysis may be used to determine if the trend for the monitored parameters/features is towards hypoglycemia. Otherwise conventional threshold-based or linear discriminator-based techniques may be exploited. In at least some embodiments, the linear discriminator is trained based on sets of data known to be representative of normal BGL or hypoglycemic BGL. The sets of data may be obtained from test populations or, in some cases, from the particular patient in which the discriminator is to be implanted. In this manner, the linear discriminator may be trained to optimize its detection specificity within any particular patient. At least some of the temporal or spectral parameters that are indicative of hypoglycemia may vary from patient to patient. Otherwise conventional techniques may be applied to train the linear discriminator to detect the particular parameters within a particular patient that are most sensitive to hypoglycemia such that the hypoglycemia detector within that patient can then be configured to detect those particular parameters, further improving specificity. Techniques for training linear discriminators or other pattern classifiers are described in the above-cited application to Bharmi et al. (Ser. No. 11/558,787), filed Nov. 10, 2006 and in U.S. patent application Ser. No. 11/394,724, filed Mar. 31, 2006, of Ke et al., entitled "Ischemia Detection Using T-wave amplitude, QTmax and ST Segment Elevation and Pattern Classification Techniques." Also, rather than be programmed to merely output an indication of whether the patient is subject to hypoglycemia, the decision logic may further indicate the severity of the episode.

Note that not all of the data obtained by the pacer/ICD within the steps of FIG. 3 need be applied to the linear discriminator. To reduce processing requirements, only some of the data, particularly data that is easy to derive from the IEGM, may initially be applied to the discriminator to make a preliminary decision. If a preliminary indication of hypoglycemia is made, then other data, such as spectral data, LF/HF ratios, etc., is calculated for use in confirming the detection. In one particular example, the LF/HF frequency based features are not initially applied to the linear discriminator but are only calculated if a preliminary indication of hypoglycemia is made so as to verify the detection. Note also that, in implementations wherein gender is input, thresholds or weights used within the decision logic may be set differently for male/female patients to improve detection specificity. In any case, if an indication of hypoglycemia is generated by the linear discriminator, a suitable alarm is issued, at step 238, and, as already explained, other action may be taken, such as control of therapy, recording of diagnostics data, etc.

Thus, various techniques have been described for detecting hypoglycemia, particularly pre-symptomatic hypoglycemia. Note that, whereas the techniques described herein are preferably employed substantially in real-time based on IEGM signals as they are sensed, the techniques can alternatively be employed based on previously recorded signals. For example, IEGM data may be collected over time then analyzed later to detect hypoglycemia for the purpose of generating appropriate diagnostic data for physician review. Such delayed analysis techniques can be performed either using the implanted device itself or using an external data processing device based on data transmitted from the implanted device. Real time detection is preferred as it allows hypoglycemia to be promptly detected so that warning can be promptly issued and therapy can be appropriately controlled, as needed. Note also that the techniques can be applied to detecting other conditions besides hypoglycemia, particularly diabetic ketoacidosis when blood sugars are very high.

For the sake of completeness, a detailed description of an exemplary pacer/ICD for performing these techniques will now be provided. However, principles of invention may be implemented within other pacer/ICD implementations or within other devices.

Exemplary Pacemaker/ICD

FIG. 8 provides a simplified block diagram of the pacer/ICD, which is a multi-chamber stimulation device capable of treating both fast and slow arrhythmias with stimulation therapy, including cardioversion, defibrillation, and pacing stimulation (as well as capable of detecting pre-symptomatic hypoglycemia as discussed above.) To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
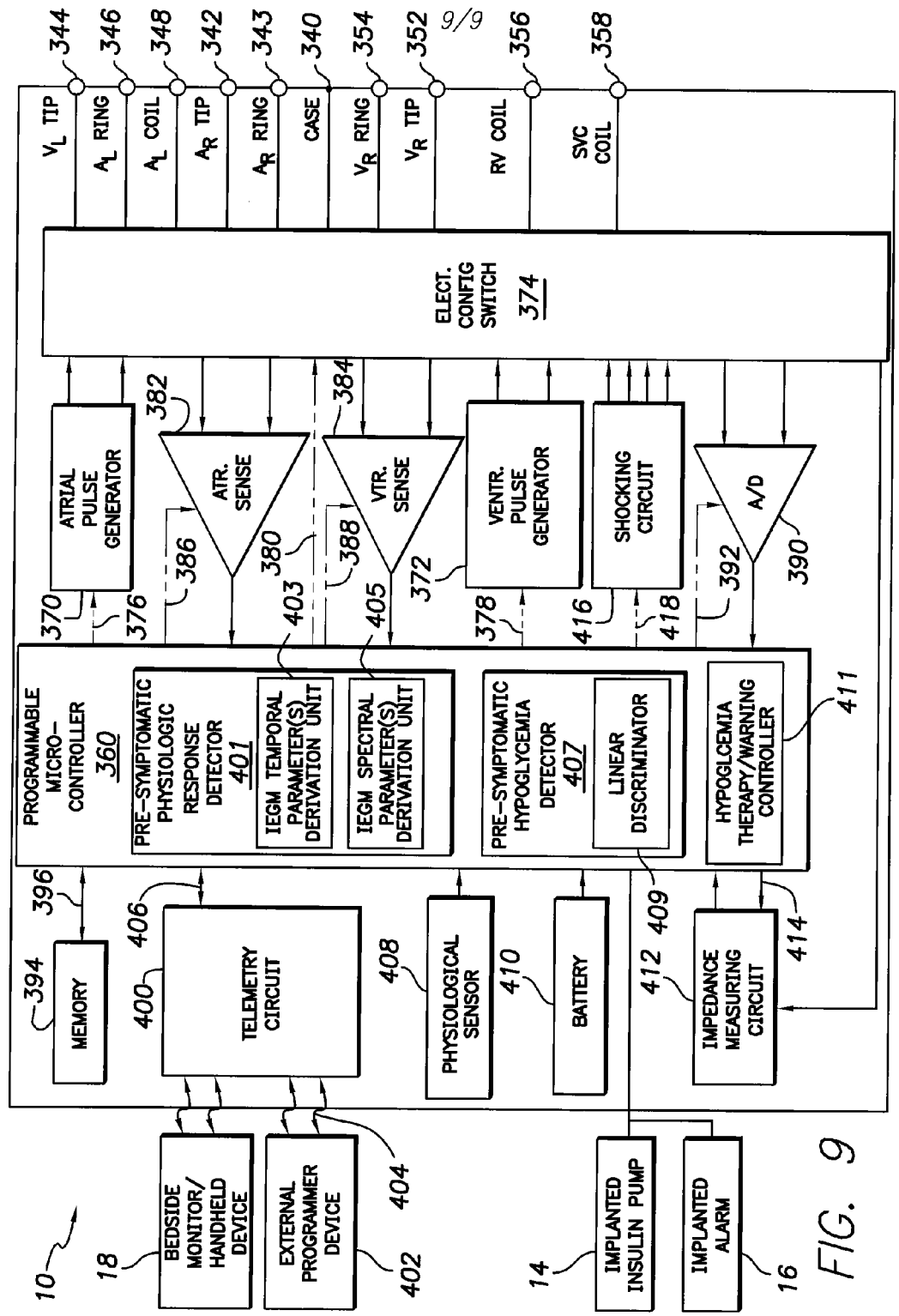
FIG. 9 is a functional block diagram of the pacer/ICD of FIG. 8, illustrating basic circuit elements that provide cardioversion, defibrillation and/or pacing stimulation in the heart and particularly illustrating components for performing the techniques of FIGS. 2-7.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 340 for pacer/ICD 10, shown schematically in FIG. 9, is often referred to as the "can", case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 343. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods (when appropriate), blanking intervals (when appropriate), noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 382 and 384, are connected to the microcontroller 360 which detects events therein and, in turn, triggers or inhibits the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals to identify the events (as already described) and to identifying the presence of an arrhythmia. The timing intervals between sensed events (e.g., P-waves, R-waves, and depolarization signals associated with fibrillation which are sometimes referred to as "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (N/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 9, pacer/ICD 10 is shown as having an impedance measuring circuit 412 which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an ICD device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 3-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components for implementing or controlling pre-symptomatic hypoglycemia detection procedures described above. In particular, the microcontroller includes a pre-symptomatic physiological response detector 401 that is operative to derive values representative of a pre-symptomatic physiologic response to a hypoglycemic event from sensed IEGM signals, as discussed above. Detector 401 includes both an IEGM temporal parameter(s) derivation unit 403 and an IEGM spectral parameter(s) derivation unit 405 to derive the various temporal or spectral parameters discussed above. The microcontroller also includes a pre-symptomatic hypoglycemia detector 407 that is operative to detect hypoglycemia based on the values representative of physiologic response detector by physiological response detector 401. In this example, hypoglycemia detector 407 includes a linear discriminator 409 but, as already explained, various other decision logic devices can instead be exploited. Warnings and therapy are controlled by hypoglycemia therapy/warning controller 411. Diagnostics information is stored within memory 394. Depending upon the implementation, the various components illustrated within the microcontroller may be implemented as separate hardware or software modules. However, the modules may be combined so as to permit single modules to perform multiple functions.

What have been described are various exemplary systems and methods for use with an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the scope of the invention. Note also that the term "including" as used herein is intended to be inclusive, i.e. "including but not limited to."

What is claimed is:

1. A method for use with an implantable medical device for detecting hypoglycemia within a patient in which the device is implanted, said method comprising:
   sensing an electrical cardiac signal;
   deriving values representative of a pre-symptomatic physiologic response to a hypoglycemic event from the cardiac signal by deriving temporal morphological parameters within the cardiac signal that are affected by pre-symptomatic hypoglycemia and deriving spectral parameters from the cardiac signal that are affected by pre-symptomatic hypoglycemia; and
   detecting hypoglycemia based on the values representative of the pre-symptomatic physiologic response.

2. The method of claim 1 wherein the temporal morphological parameters include one or more of: T-wave morphological parameters; P-wave morphological parameters; QRS morphological parameters; far-field waveform morphological parameters; QT dynamics parameters; heart rate parameters; paced depolarization integrals (PDIs) and T-wave integrals.

3. The method of claim 1 wherein the temporal morphological parameters derived from the cardiac signal include one or more of: respiration rate and respiration depth.

4. The method of claim 1 wherein deriving values representative of the pre-symptomatic physiologic response includes deriving parameters representative of one or more of the mean, standard deviation and variance of the values.

5. The method of claim 1 wherein deriving values representative of the pre-symptomatic physiologic response includes deriving parameters representative of trends within the values.

6. The method of claim 1 wherein deriving spectral parameters from the cardiac signal includes first deriving temporal parameters from the cardiac signal that are affected by pre-symptomatic hypoglycemia and then deriving spectral characteristics from the temporal parameters.

7. The method of claim 6 wherein deriving spectral parameters includes applying a Fast Fourier Transform (FFT) to the temporal parameters.

8. The method of claim 1 wherein deriving spectral parameters includes deriving a mean spectral power.

9. The method of claim 1 wherein deriving spectral parameters includes determining a ratio of relatively low frequency components to relatively high frequency components of the cardiac signal.

10. The method of claim 1 wherein detecting hypoglycemia based on the values representative of the pre-symptomatic physiologic response includes detecting hypoglycemia based on a combination of temporal parameters derived from the cardiac signals and spectral parameters derived from the cardiac signal.

11. The method of claim 1 wherein detecting hypoglycemia based on the values representative of the pre-symptomatic physiologic response includes applying the values to decision logic programmed to recognize hypoglycemia based on the values.

12. The method of claim 11 wherein applying the values to decision logic includes applying the values to a linear discriminator programmed to recognize hypoglycemia based on the values.

13. The method of claim 11 wherein applying the values to the decision logic includes the initial step of detecting and eliminating outliers within the values.

14. The method of claim 11 wherein applying the values to the decision logic includes the initial steps of detecting patient body position and normalizing the values based on body position.

15. The method of claim 11 wherein applying the values to the decision logic includes the initial steps of detecting cardiac rhythm type within the patient and normalizing the values based on rhythm type.

16. The method of claim 11 wherein applying the values to the decision logic includes the initial steps of detecting patient activity level and normalizing the values based on activity level.

17. The method of claim 1 further including inputting the gender of the patient and wherein detecting hypoglycemia is performed based on the values representative of the pre-symptomatic physiologic response and patient gender.

18. The method of claim 1 further including inputting aspects of patient history for the patient and wherein detecting hypoglycemia is performed based on the values representative of the pre-symptomatic physiologic response and patient history.

19. The method of claim 18 further including monitoring for symptoms of hypoglycemia and wherein detecting hypoglycemia is performed based on values representative of the pre-symptomatic physiologic response and information pertaining to symptoms, if any, of hypoglycemia.

20. The method of claim 19 wherein monitoring for symptoms of hypoglycemia includes detecting episodes of tachycardia within the patient.

21. The method of claim 19 wherein monitoring for symptoms of hypoglycemia includes detecting tremors within the patient.

22. The method of claim 19 wherein monitoring for symptoms of hypoglycemia includes inputting information pertaining to symptoms from an external device.

23. The method of claim 19 wherein monitoring for symptoms of hypoglycemia includes inputting from an external device, information pertaining to one or more of the following symptoms: excessive perspiration, tremors, skin pallor, anxiety, hunger, warmth, light-headedness, weakness, headache, confusion, lack of coordination, and speech difficulty.

24. The method of claim 1 further including the step of detecting blood glucose levels within the patient and wherein detecting hypoglycemia includes detecting hypoglycemia based on a combination of the values representative of the pre-symptomatic physiologic response and blood glucose levels.

25. The method of claim 1 including recording diagnostic information based on the detection of hypoglycemia, wherein the diagnostic information includes trends, if any, in the values representative of the pre-symptomatic physiologic response to the hypoglycemic event.

26. A system for use with an implantable medical device for detecting hypoglycemia within a patient in which the device is implanted, said system comprising:
  an electrical cardiac signal detector operative to detect an electrical cardiac signal within the patient;
  a pre-symptomatic physiologic response detector operative to derive values representative of a pre-symptomatic physiologic response to a hypoglycemic event from the cardiac signal by deriving temporal morphological parameters within the cardiac signal that are affected by pre-symptomatic hypoglycemia and deriving spectral parameters from the cardiac signal that are affected by pre-symptomatic hypoglycemia; and
  a hypoglycemia detector operative to detect hypoglycemia based on the values representative of a pre-symptomatic physiologic response to a hypoglycemic event.

27. A system for use with an implantable medical device for detecting hypoglycemia within a patient in which the device is implanted, said system comprising:
  means for detecting an electrical cardiac signal within the patient;
  means for deriving values representative of a pre-symptomatic physiologic response to a hypoglycemic event from the cardiac signal by deriving temporal morphological parameters within the cardiac signal that are affected by pre-symptomatic hypoglycemia and deriving spectral parameters from the cardiac signal that are affected by pre-symptomatic hypoglycemia; and
  means for detecting hypoglycemia based on the values representative of a pre-symptomatic physiologic response to a hypoglycemic event.

* * * * *